(12) United States Patent
Klimko

(10) Patent No.: US 6,417,228 B1
(45) Date of Patent: Jul. 9, 2002

(54) 13-AZA PROSTAGLANDINS FOR THE TREATMENT OF GLAUCOMA AND OCULAR HYPERTENSION

(75) Inventor: Peter G. Klimko, Fort Worth, TX (US)

(73) Assignee: Alcon Manufacturing, Ltd.., Fort Worth, TX (US)

( * ) Notice: Subject to any disclaimer, the term of this patent is extended or adjusted under 35 U.S.C. 154(b) by 0 days.

(21) Appl. No.: 09/430,513

(22) Filed: Oct. 29, 1999

Related U.S. Application Data

(60) Provisional application No. 60/106,731, filed on Nov. 2, 1998.

(51) Int. Cl.$^7$ .................... A61K 31/215; A61K 31/557; C07C 229/00
(52) U.S. Cl. ................... 514/530; 514/573; 560/48; 562/457
(58) Field of Search ................ 514/530, 573; 560/48; 562/457

(56) References Cited

U.S. PATENT DOCUMENTS

| | | | |
|---|---|---|---|
| 4,182,903 A | 1/1980 | Favara et al. | 562/503 |
| 4,189,606 A | 2/1980 | Favara et al. | 562/455 |
| 4,265,891 A | * 5/1981 | Collington et al. | 424/244 |
| 4,599,353 A | 7/1986 | Bito | 514/236.2 |
| 4,952,581 A | 8/1990 | Bito et al. | 514/530 |
| 5,321,128 A | 6/1994 | Stjernschantz et al. | 514/530 |
| 5,773,471 A | 6/1998 | Oguchi et al. | 514/530 |
| 5,811,443 A | 9/1998 | DeSantis et al. | 514/392 |

FOREIGN PATENT DOCUMENTS

| | | |
|---|---|---|
| DE | 4229050 A1 | 3/1994 |
| EP | 0561073 A1 | 9/1993 |
| NL | 7905375 * | 1/1980 |

OTHER PUBLICATIONS

Glaxo Group. Dutch patent application NL 1979–5375 (abstract) CAPLUS (online) (retrieved May 16, 2000) Retrieved from STN International, Columbus OH USA. Accession No. 1980:494884, Jan. 1980.*

Alm, The Potential of Prostaglandin Derivatives in Glaucoma Therapy, *Current Opinion in Ophthalmology* 4(11):44–50 (1993).

Favara, et al., Synthesis and Antifertility Activity of 13–Aza 14–Oxo–Prostaglandins *Prostaglandins* 25(3):311–320 (1983).

Giuffre, The Effects of Prostaglandin $F_{2\alpha}$ in the Human Eye, *Graefe's Arch Clin Exp Ophthalmol* 222:139–141 (1985).

Kerstetter et al., Prostaglandin $F_{2\alpha}$–1–Isopropylester Lowers Intraocular Pressure Without Decreasing Aqueous Humor Flow, *American Journal of Ophthalmology* 105:30–34 (1988).

Nakajima et al., Effects of Prostaglandin $D_2$ and its analogue, BW245C, on Intraocular Pressure in Humans, *Graefe's Arch Clin Exp Ophthalmol* 229:411–413 (1991).

* cited by examiner

*Primary Examiner*—Howard C. Lee
*Assistant Examiner*—Leigh C. Maier
(74) *Attorney, Agent, or Firm*—Barry L. Copeland

(57) ABSTRACT

13-Aza analogs of $PGF_{2\alpha}$ and methods of their use in treating glaucoma and ocular hypertension are disclosed.

19 Claims, No Drawings

13-AZA PROSTAGLANDINS FOR THE TREATMENT OF GLAUCOMA AND OCULAR HYPERTENSION

CROSS REFERENCE TO RELATED APPLICATIONS

This application draws priority from U.S. Provisional Application Ser. No. 60/106,731 filed Nov. 2, 1998.

BACKGROUND OF THE INVENTION

The present invention relates to novel compounds and methods for the treatment of glaucoma and ocular hypertension. In particular, the present invention relates to the use of certain 13-aza analogs of F series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art a being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (EP 0 561 073 A1). Of interest in the present invention are compounds which are believed to exhibit IOP lowering mechanisms similar to those exhibited by $PGF_{2\alpha}$ (an F-series prostaglandin);

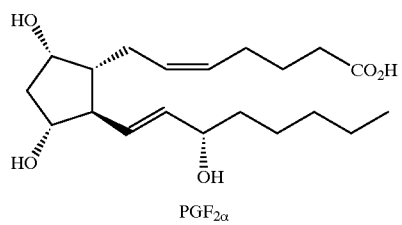

$PGF_{2\alpha}$

The relationship of $PGF_{2\alpha}$ receptor activation and IOP lowering effects is not well understood. It is believed that $PGF_{2\alpha}$ receptor activation leads to increased outflow of aqueous humor. Regardless of the mechanism, $PGF_{2\alpha}$ and certain of its analogs have been shown to lower IOP (Giuffre, *The Effects of Prostaglandin $F_{2\alpha}$ the Human Eye*, Graefe's Archive Ophthalmology, volume 222, pages 139–141 (1985); and Kerstetter et al., *Prostaglandin $F_{2\alpha}$-1-Isopropylester Lowers Intraocular Pressure Without Decreasing Aqueous Humor Flow*, American Journal of Ophthalmology, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (Graefe's Archive Ophthalmology, volume 229, pages 411–413 (1991)). Though $PGF_{2\alpha}$-type molecules lower IOP, a number of these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy*, Current Opinion in Ophthalmology, volume 4, No. 11, pages 44–50 (1993)).

Based on the foregoing, a need exists for the development of molecules that may activate the $PGF_{2\alpha}$ receptor yielding a more efficacious lowering of IOP, while exhibiting fewer or reduced side effects.

An agent which exhibits comparable or improved efficacy, but with reduced side effects when compared to other agents, is said to have an improved therapeutic profile. It is an object of this invention to provide a class of IOP lowering agents with an improved therapeutic profile over $PGF_{2\alpha}$ and methods of their use. It has now unexpectedly been discovered that the presently claimed 13-aza analogs of prostaglandins meet this objective. Although several 13-aza compounds of the present invention of formula i below are known [Favara, D.; et. al. *Prostaglandins* 1983, 25(3), 311; and U.S. Pat. Nos. 4,189,606 and 4,182,903 the disclosures of which are by this reference incorporated herein], we are aware of no reports teaching or suggesting their IOP-lowering abilities.

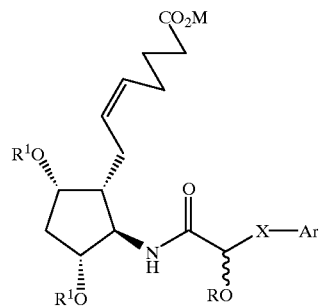

i wherein: M=H, alkyl, or cation; $R^1$=acyl or H; R=H or alkyl; $X=CH_2O$ or $(CH2)n$, where n=0–4; and Ar=substituted or unsubstituted phenyl.

SUMMARY OF THE INVENTION

The present invention is directed to novel compounds and compositions, and methods of their use, as well as the novel use of some known compounds, in treating glaucoma and ocular hypertension. In particular, the present invention provides 13-aza prostaglandins having functional $PGF_{2\alpha}$ receptor agonist activity, and methods of their use in treating glaucoma and ocular hypertension.

DETAILED DESCRIPTION OF THE INVENTION

It has unexpectedly been found that 13-aza prostaglandin analogs of the present invention exhibit an improved therapeutic profile in the treatment of glaucoma and ocular hypertension when compared to natural prostaglandins and many of their known analogs. The 13-aza prostaglandin analogs of the present invention may also be used to treat optic nerve disorder by retarding visual field loss or improving visual acuity in the manner described in U.S. Pat. No. 5,773,471, the disclosure of which is incorporated herein by this reference.

It is further contemplated that the compounds of the present inventions can be used with other medicaments known to be useful in the treatment of glaucoma or ocular hypertension, either separately or in combination. For example, the 13-aza prostaglandin analogs of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivative;, such as apraclonidine or brimonidine (see U.S. Pat. No. 5,811,443); and (iv) cholinergic agonists, such as pilocarpine. The disclosures of U.S. Pat. Nos. 4,952,581 and 5,811,443 are incorporated herein by this reference.

The 13-aza prostaglandin analogs of the present invention have the following formula I:

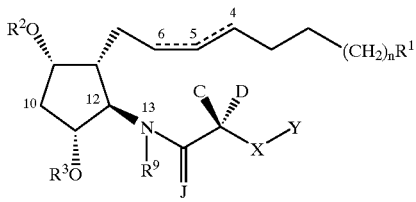

wherein:
$R^1 = CO_2R$, $CONR^4R^5$, $CH_2OR^6$, or $CH_2NR^7R^8$, where:
R=H, alkyl, cationic salt moiety, or $CO_2R$ forms a pharmaceutically acceptable ester moiety;
$R^4$, $R^5$=same or different=H or alkyl;
$R^6$=H, acyl, or alkyl; and
$R^7$, $R^8$=same or different=H, acyl, or alkyl; with the proviso that if one of $R^7$, $R^8$=acyl, then the other=H or alkyl;
n=0 or 2;
$R^2$, $R^3$=same or different=H, alkyl, or acyl;
―――=single or non-cumulated double bond;
J=O or H and H;
$R^9$=H, alkyl, acyl, or $SO_2Ar$, where Ar=a phenyl ring optionally substituted with hydroxy, acyloxy, alkoxy, alkoxycarbonyl, halo, trihalomethyl, amino, acylamino, or aminoacyl;
one of C,D=H, and the other=F,OH, acyloxy, or alkoxy;
or C―D=O$(CH_2)_2$O or double bond O;
with the proviso that if J=O then $R^9$=H or alkyl, and one of C, D=H, and the other=F, OH, acyloxy, or alkoxy;
$X=(CH_2)_q$, or $(CH_2)_qO$; where q=0–6; and
Y=a phenyl ring optionally substituted with alkyl, halo, trihalomethyl, alkoxy, acyl, acyloxy, alkylamino, acylamino, or OH;
or $X—Y=(CH_2)_pY^1$, where p=0–6 and

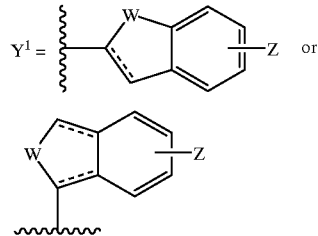

wherein:
$W=CH_2$, O, $S(O)_m$, $NR^{10}$, $CH_2CH_2$, CH=CH, $CH_2O$, $CH_2S(O)_m$, CH=N, or $CH_2NR^{10}$, where m=0–2, and $R^{10}$=H, alkyl, or acyl;
Z=H, alkyl, alkoxy, acyl, acyloxy, halo, trihalomethyl, amino, alkylamino, acylamino, or OH; and
―――=single or double bond.

As used herein, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e. non-toxic and non-irritating. Preferred are alkyl esters. Most preferred are $C_2$–$C_4$ alkyl esters, and especially isopropyl esters.

Preferred compounds for use in the present invention are those of formula I above, wherein:
$R^1=CO_2R$, where R=H, or $CO_2R$ forms an ophthalmically acceptable ester moiety;
n=0;
$R^2=R^3=H$;
―――=single or non-cumulated double bond, with the proviso that a double bond between carbons 4 and 5 may not be of the trans configuration:
J=O, or H and H;
$R^9$=H when J=O; and $R^9$=H or acyl when J=H and H;
one of C, D=H, and the other=OH;
$X=(CH_2)_2$ or $CH_2O$; and
Y=phenyl, optionally substituted with halo or trihalomethyl; or
$X—Y=Y^1$ where

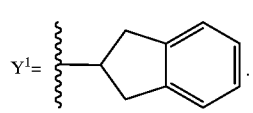

Most preferred for use in the present invention are the following compounds:

| Compound Number | Compound Name | Compound Structure |
|---|---|---|
| II | (5Z)-(9S,11R,15R)-13-Aza-16-(4-fluorophenoxy)-14-oxo-9,11,15-trihydroxy-17,18,19,20-tetranor-5-prostenoic acid isopropyl ester | 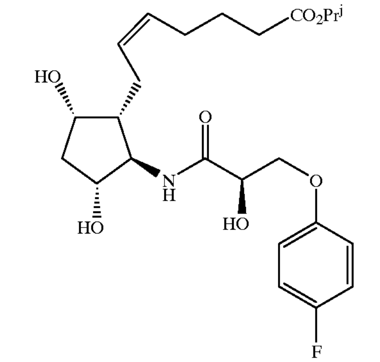 |
| III | (4Z)-(9S,11R,15R)-13-Aza-16-(4-fluorophenoxy)-14-oxo-9,11,15-trihydroxy-17,18,19,20-tetranor4-prostenoic acid isopropyl ester | 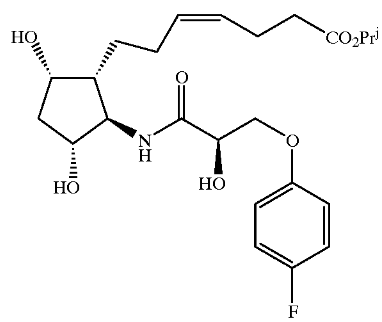 |
| IV | (5Z)-(9S,11R,15R)-13-Aza-17-(4-fluorophenyl)-14-oxo-9,11,15-trihydroxy-18,19,20-trinor-5-prostenoic acid isopropyl ester | 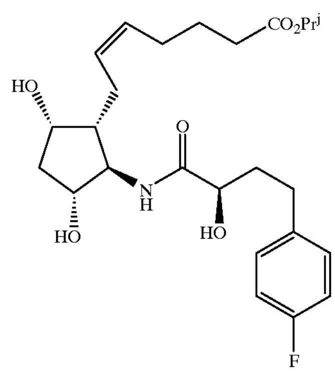 |
| V | (5Z)-(9S,11R,15R)-13-Aza-17-(4-fluorophenyl)-9,11,15-trihydroxy-18,19,20-trinor-5-prostenoic acid isopropyl ester | 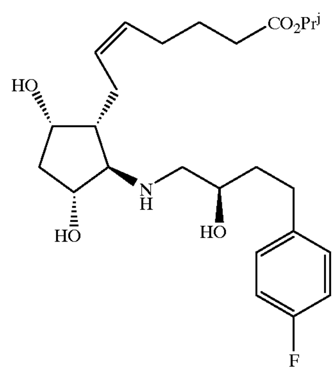 |

The compounds of the present invention believed to be novel are those compounds of formula I wherein:

$R^1$=$CO_2R$, $CONR^4R^5$, $CH_2OR^6$, or $CH_2NR^7R^8$, where:

R=H, alkyl, cationic salt moiety, or $CO_2R$ forms a pharmaceutically acceptable ester moiety;

$R^4$, $R^5$=same or different=H or alkyl;

$R^6$=H, acyl, or alkyl; and $R^7$, $R^8$=same or different=H, acyl, or alkyl; with the proviso that if one of $R^7$, $R^8$=acyl, then the other=H or alkyl;

n=0 or 2;

$R^2$, $R^3$=same or different=H, alkyl, or acyl;

———=single or non-cumulated double bond;

J=O or H and H;

$R^9$=H, alkyl, acyl, or $SO_2Ar$, where Ar=a phenyl ring optionally substituted with hydroxy, acyloxy, alkoxy, alkoxycarbonyl, halo, trihalomethyl, amino, acylamino, or aminoacyl;

one of C, D=H, the other=F, OH, acyloxy, or alkoxy; or

C—D=O$(CH_2)_2$O or double bonded O;

with the proviso that if J=O, then $R^9$=H or alkyl, one of C, D=H, and the other=F, OH, acyloxy, or alkoxy;

X=$(CH_2)_q$ or $(CH_2)_q$O, where q=0–6; and

Y=a phenyl ring optionally substituted with alkyl, halo, trihalomethyl, alkoxy, acyl, acyloxy, alkylamino, acylamino, or OH; or X—Y=$(CH_2)_p Y^1$, where p=0–6 and

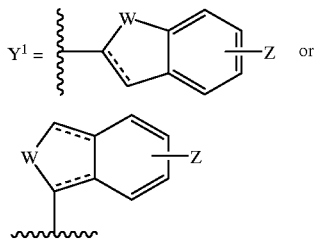

wherein:

W=$CH_2$, O, $S(O)_m$, $NR^{10}$, $CH_2CH_2$, CH=CH, $CH_2O$, $CH_2S(O)_m$, CH=N, or $CH_2NR^{10}$, where m=0.2; and $R^{10}$=H, alkyl, acyl;

Z=H, alkyl, alkoxy, acyl, acyloxy, halo, trihalomethyl, amino, alkylamino, acylamino, or OH; and ———=single or double bond;

with the proviso that the compounds of formula I possessing all of the following limitations be excluded:

$R^1$=$CO_2R$, where R=H, alkyl, or cationic salt moiety;

n=0;

———=a single bond between carbons 4 and 5, and a cis double bond between carbons 5 and 6;

$R^2$, $R^3$=H or acyl;

$R^9$=H;

J=O;

one of C,D=H, and the other=OH or alkoxy;

X=$(CH_2)_q$ or $(CH_2)_q$O, where q=0–6; and

Y=a phenyl ring optionally substituted with alkyl, halo, trihalomethyl, alkoxy, acyl, acyloxy, alkylamino, acylamino, or OH.

Preferred novel compounds of the invention include those of formula I, wherein:

$R^1$=$CO_2R$, where R=H or $CO_2R$ forms a pharmaceutically acceptable ester moiety;

n=0;

———=a single bond between carbons 5 and 6, and a cis double bond between carbons 4 and 5; or a single bond between carbons 4 and 5, and a cis double bond between carbons 5 and 6;

$R^2$=$R^3$=H;

$R^9$=H;

J=O or H and H;

one of C,D=H, and the other=OH;

X=$CH_2$O or $CH_2CH_2$; and

Y=phenyl, optionally substituted with halo or trihalomethyl; or

X—Y=$Y^1$, where

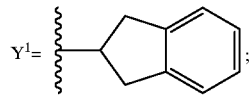

with the proviso that the compounds of formula I possessing all of the following limitations be excluded, wherein:

$R^1$=$CO_2R$, where R=H;

n=0;

———=a single bond between carbons 4 and 5, and a cis double bond between carbons 5 and 6;

$R^2$=$R^3$=H;

$R^9$=H;

J=O;

one of C,D=H, and the other=OH;

X=$CH_2$O or $CH_2CH_2$; and

Y=phenyl, optionally substituted with halo or trihalomethyl.

Chemical Definitions

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1 -methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "cationic salt moiety" includes alkali and alkaline earth metal salts as well as ammonium salts.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cyclopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

In the foregoing illustrations, as well as those provided hereinafter, wavy line attachments indicate that the configuration may be either alpha (α) or beta (β). The carbon numbering is as indicated in formula I, even when n=2. Dashed lines on bonds indicate a single or double bond. Two solid lines between carbons specify the configuration of the relevant double bond. Hatched lines indicate the α configuration. A solid triangular line indicates the β configuration.

In the following Examples 1–4, the following standard abbreviations are used: g=grams (mg=milligrams); mol= moles (mmol=millimoles); mL=milliliters; mm Hg=millimeters of mercury; mp=melting point; bp=boiling point; h=hours, and min=minutes. In addition, "NMR" refers to nuclear magnetic resonance spectroscopy and "MS" refers to mass spectrometry.

EXAMPLE 1

Synthesis of II

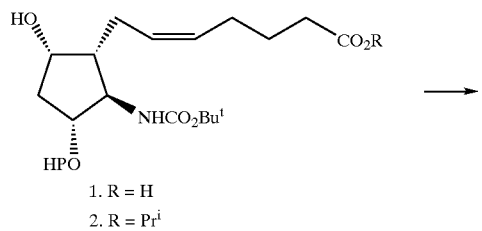

1. R = H
2. R = Pr$^i$

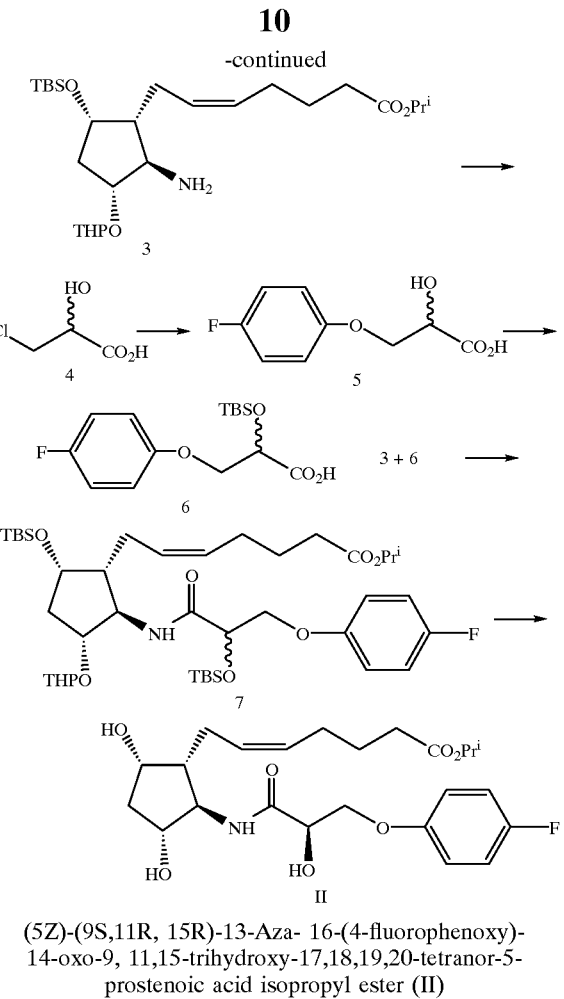

(5Z)-(9S,11R, 15R)-13-Aza- 16-(4-fluorophenoxy)-14-oxo-9, 11,15-trihydroxy-17,18,19,20-tetranor-5-prostenoic acid isopropyl ester (II)

Acid 1 [for the synthesis of 1, see *Prostaglandins* 1983, 25(3), 311] is treated with isopropyl iodide and 1,8-diazabicyclo[5.4.0]undec-7-ene (DBU) in acetone to afford isopropyl ester 2. Treatment of 2 with t-butyldimethylsilyl trifluoromethanesulfonate (TBSOTf) and 2,6-lutidine in $CH_2Cl_2$, followed by tetra-n-butylammonium fluoride (TBAF) in tetrahydrofuran (THF), provides amine 3. Reaction of p-fluorophenol and β-chlorolactic acid (4) in hot aqueous sodium hydroxide affords acid 5, which is treated sequentially with excess t-butyldimethylsilyl chloride and methanol/acetic acid/water to provide siloxyacid 6. Coupling of 3 and 6 in the presence of diphenylphosphoryl azide (DPA) provides amide 7, which is deprotected using HCl/water/isopropanol to afford II after chromatographic separation of the carbon 15 diastereomers.

EXAMPLE 2

Synthesis of III

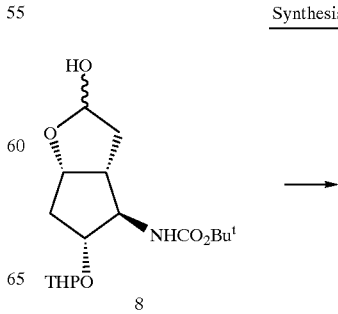

8

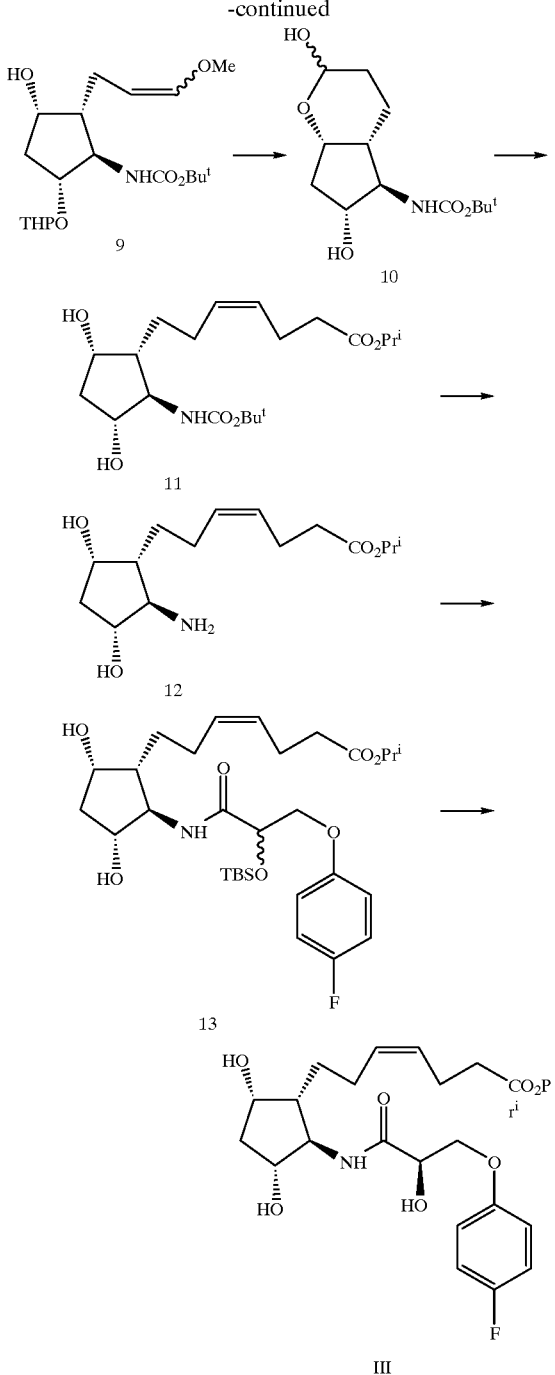

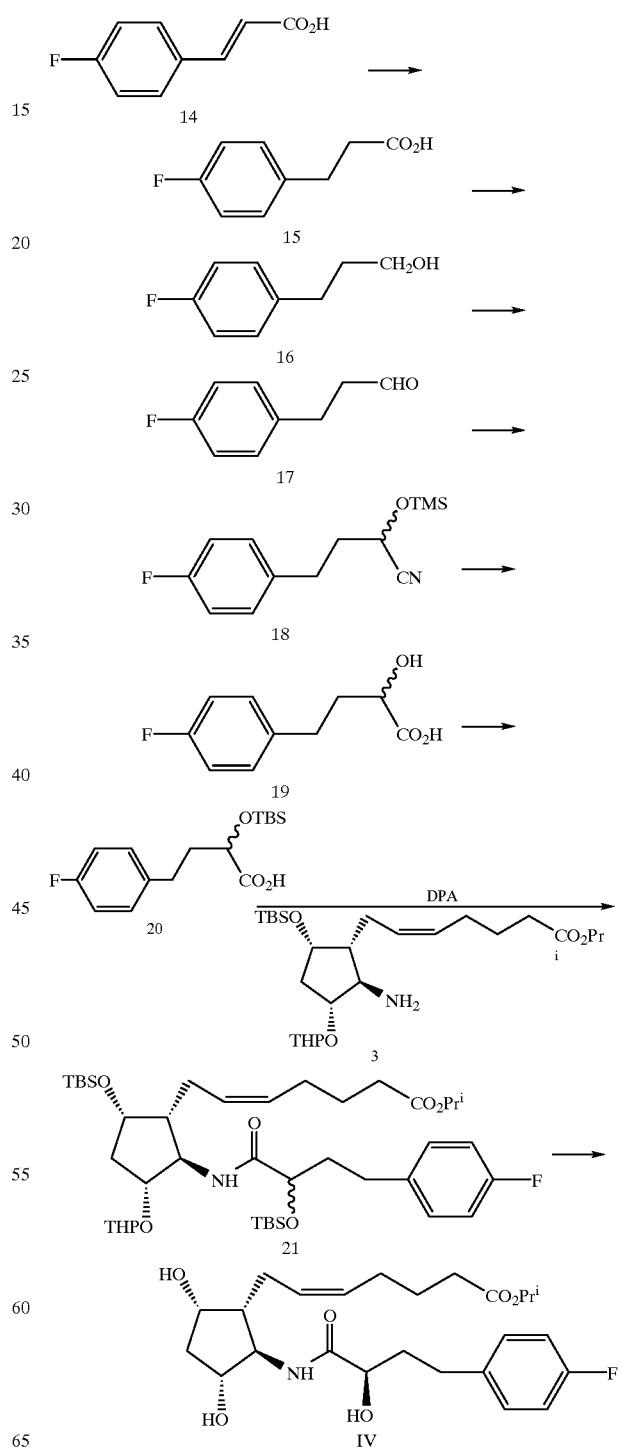

(4Z)-(9S,11R,15R)-13-Aza-16-(4-fluorophenoxy)-14-oxo-9,11,15-trihydroxy- 17,18,19,20-tetranor-4-prostenoic acid isopropyl ester (III)

Lactol 8 [for the synthesis of 8, see *Prostaglandins* 1983, 25(3), 311] is condensed with $Ph_3P^+CH_2OCH_3\ Cl^-$ in THF in the presence of potassium t-butoxide to afford enol ether 9. Conversion of 9 to lactol 10 is effected using HCl in aqueous isopropanol. Reaction of 10 with $Ph_3P^+(CH_2)_3CO_2H\ Br^-$ in THF in the presence of potassium t-butoxide, followed by isolation of the product olefin acid and esterification with isopropyl iodide in the acetone in presence of DBU, provides ester 11. Treatment of 11 with TBSOTf and 2,6-lutidine in $CH_2Cl_2$, followed by addition of TBAF in THF, yields amine 12. DPA-mediated coupling of 12 with acid 6 gives amide 13, which is deprotected with TBAF in THF to afford III after chromatographic separation of the carbon 15 diastereomers.

EXAMPLE 3

Synthesis of IV

(5Z)-(9S,11R,15R)-13-Aza-17-(4-fluorophenyl)-14-oxo-9,11,15-trihydroxy-18,19,20-trinor-5-prostenoic acid isopropyl ester (IV)

Hydrogenation of p-fluorocinnamic acid (14) in methanol using palladium on charcoal catalyst affords hydrocinnamic acid 15. Reduction of 15 with $BH_3$:dimethyl sulfide complex provides alcohol 16, which is oxidized using oxalyl chloride/dimethyl sulfoxide to afford aldehyde 17. Addition of trimethylsilyl cyanide to 17 gives silylated cyanohydrin 18, which is hydrolyzed using HCl to provide hydroxyacid 19. Treatment of 19 with t-butyldimethylsilyl chloride, followed by methanol/acetic acid/water, yields siloxyacid 20. Condensation of 20 with amine 3 in the presence of DPA gives amide 21, which is deprotected using HCl in aqueous isopropanol to afford IV after chromatographic separation of the carbon 15 diastereomers.

EXAMPLE 4

Synthesis of V

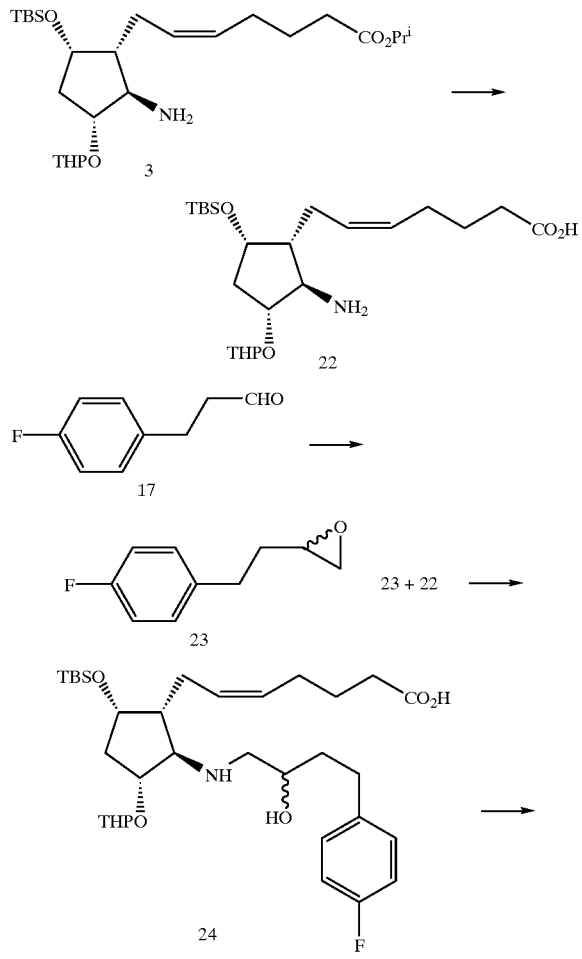

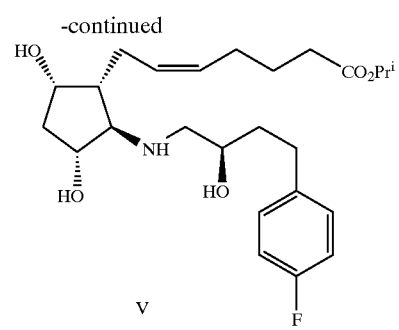

(5Z)-(9S,11R,15R)-13-Aza-17-(4-fluorophenyl)-9,11,15-trihydroxy-18,19,20-trinor-5-prostenoic acid isopropyl ester (V)

Saponification of ester 3 with lithium hydroxide in methanol/water provides amino acid 22. Treatment of aldehyde 17 with $Me_3S^+$ $I^-$ in the presence of NaH affords epoxide 23. Addition of 22 to 23 in the presence of potassium carbonate gives aminoalcohol 24, which is deprotected and esterified in one pot by treatment with $H_2SO_4$ in isopropanol to provide V after chromatographic separation of the carbon 15 diastereomers.

The 13-aza prostaglandin analogs of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0, preferably between about 7.0 and 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting is solution be topically applied by placing one drop in each eye one or two times a day.

Other ingredients which may be desirable to use in the ophthalmic preparations of the present invention include preservatives, co-solvents, and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methyl cellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of the cyclohexyl prostaglandins of the present invention include the following Examples 5–7:

EXAMPLE 5

| Ingredient | Amount (wt %) |
|---|---|
| Compound II | 0.01 |
| Phosphate Buffered Saline | 1.0 |
| Polysorbate 80 | 0.5 |
| Purified water | q.s. to 100% |

EXAMPLE 6

| Ingredient | Amount (wt %) |
|---|---|
| Compound III | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 7

| Ingredient | Amount (wt %) |
|---|---|
| Compound IV | 0.1 |
| Phosphate Buffered Saline | 1.0 |
| Hydroxypropyl-β-cyclodextrin | 4.0 |
| Purified water | q.s. to 100% |

Included within the scope of the present invention are the individual enantiomers of the title compounds substantially free of their respective antimers, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis* by J. D. Morrison and J. W. Scott, Ed., Academic Press Publishers: New York, 1983–1985 (five volumes published over a three year span with chapters contributed by about two dozen authors) and *Principles of Asymmetric Synthesis* by R. E. Gawley and J. Aube, Ed., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed., VCH Publishers: New York, 1994; *Chiral Separations* by HPLC, A. M. Krstulovic, Ed., Ellis Horwood Ltd. Publishers, 1989), or by enantioselective hydrolysis of a carboxylic acid ester sample by an enzyme (Ohno, M. Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of formula I:

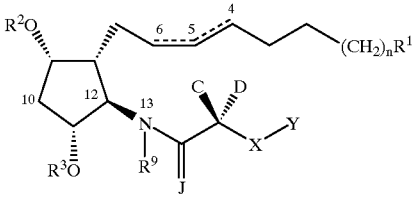

wherein:

R$^1$=CO$_2$R, CONR$^4$R$^5$, CH$_2$OR$^6$, or CH$_2$NR$^7$R$^8$, where:
  R=H, alkyl, cationic salt moiety, or CO$_2$R forms a pharmaceutically acceptable ester moiety;
  R$^4$, R$^5$=same or different=H or alkyl;
  R$^6$=H, acyl, or alkyl;
  R$^7$, R$^8$=same or different=H, acyl, or alkyl; with the proviso that if one of R$^7$, R$^8$=acyl, then the other=H or alkyl;

n=0 or 2;

R$^2$, R$^3$=same or different=H, alkyl, or acyl;

≡≡≡≡=single or non-cumulated double bond;

J=O, or H and H;

R$^9$=H, alkyl, acyl, or SO$_2$Ar, where Ar=a phenyl ring optionally substituted with hydroxy, acyloxy, alkoxy, alkoxycarbonyl, halo, trihalomethyl, amino, acylamino, or aminoacyl;

one of C, D=H, the other=F, OH, acyloxy, or alkoxy;

or C—D=O(CH$_2$)$_2$O or double bonded O;

with the proviso that if J=O, then R$^9$=H or alkyl, one of C, D=H, and the other=F, OH, acyloxy, or alkoxy;

X=$(CH_2)_q$, $(CH_2)_qO$, where q=0–6; and

Y=a phenyl ring optionally substituted with alkyl, halo, trihalomethyl, alkoxy, acyl, acyloxy, alkylamino, acylamino, or OH;

or X-Y=$(CH_2)_pY^1$, where p=0–6, and

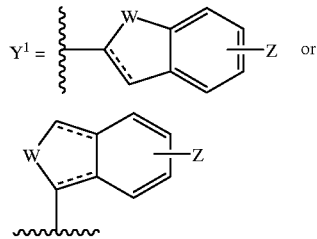

wherein:

W=$CH_2$, O, $S(O)_m$, $NR^{10}$, $CH_2CH_2$, CH=CH, $CH_2O$, $CH_2S(O)_m$, CH=N, or $CH_2NR^{10}$, where m=0–2; and $R^{10}$=H, alkyl, or acyl, Z=H, alkyl, alkoxy, acyl, acyloxy, halo, trihalomethyl, amino, alkylamino, acylamino, or OH, and ―――=single or double bond.

2. The method of claim 1, wherein the compound is administered topically.

3. The method of claim 2, wherein the compound is administered as a solution, suspension, or emulsion in an ophthalmnically acceptable vehicle.

4. The method of claim 3, wherein the concentration of the compound is between about 0.00003 to about 0.5 weight percent.

5. The method of claim 4, wherein the concentration of the compound is between about 0.0005 to about 0.03 weight percent.

6. The method of claim 5, wherein the concentration of the compound is between about 0.001 to about 0.01 weight percent.

7. The method of claim 1, wherein for the compound of formula I:

$R^1$=$CO_2R$, where R=H or $CO_2R$ forms a pharmaceutically acceptable ester moiety that is ophthalmically acceptable;

n=0;

$R^2$=$R^3$=H;

―――=single or non-cumulated double bond, with the proviso that a double bond between carbons 4 and 5 may not be of the trans configuration;

J=O, or H and H;

$R^9$=H when J=O; and $R^9$=H or acyl when J=H and H;

one of C, D=H, and the other=OH;

X=$(CH_2)_2$ or $CH_2O$; and

Y=phenyl, optionally substituted with halo or trihalomethyl; or

X-Y=$Y^1$, where

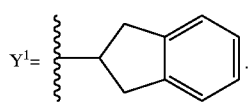

8. The method of claim 7, wherein the compound is:

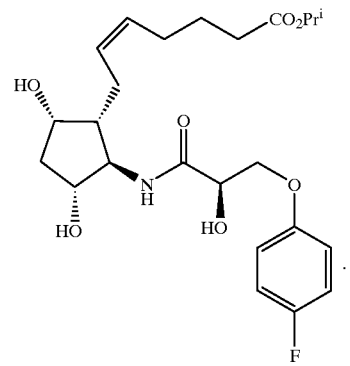

9. The method of claim 7, wherein the compound is:

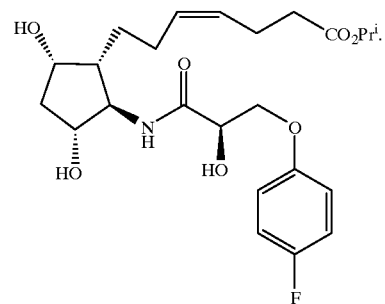

10. The method of claim 7, wherein the compound is:

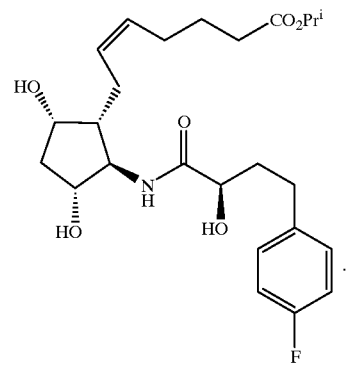

11. The method of claim 7, wherein the compound is:

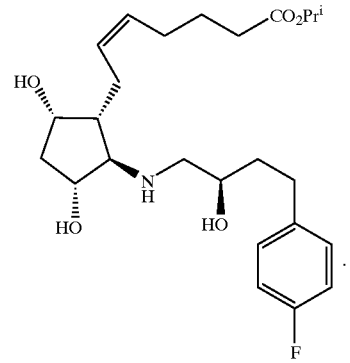

12. A compound of formula I:

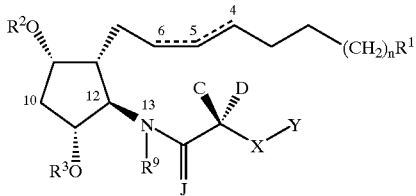

wherein:
$R^1$=$CO_2R$, $CONR^4R^5$, $CH_2OR^6$, or $CH_2NR^7R^8$, where:
R=H, alkyl, cationic salt moiety, or pharmaceutically acceptable ester;
$R^4$, $R^5$=same or different=H or alkyl;
$R^6$=H, acyl, or alkyl; and
$R^7$, $R^8$=same or different=H, acyl, or alkyl; with the proviso that if one of $R^7$, $R^8$=acyl, then the other=H or alkyl;
n=0 or 2;
$R^2$, $R^3$=same or different=H, alkyl, or acyl;
⎯⎯⎯⎯=a single bond between carbons 5 and 6 and a double bond between carbons 4 and 5;
J=O or H and H;
$R^9$=H, alkyl, acyl, or $SO_2Ar$, where Ar=a phenyl ring optionally substituted with hydroxy, acyloxy, alkoxy, alkoxycarbonyl, halo, trihalomethyl, amino, acylamino, or aminoacyl;
one of C, D=H, the other=F, OH, acyloxy, or alkoxy; or
C—D=$O(CH_2)_2O$ or double bonded O;
with the proviso that if J=O, then $R^9$=H or alkyl, one of C, D=H, and the other=F, OH, acyloxy, or alkoxy;
X=$(CH_2)_q$, or $(CH_2)_qO$, where q=0–6; and
Y=a phenyl ring optionally substituted with alkyl, halo, trihalomethyl, alkoxy, acyl, acyloxy, alkylamino, acylamino, or OH; or
X-Y=$(CH_2)_pY^1$, where p=0–6 and

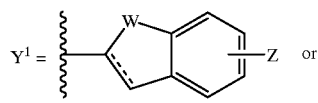 or

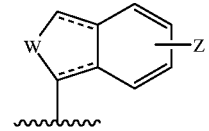

wherein:
W=$CH_2$, O $S(O)_m$, $NR^{10}$, $CH_2CH_2$, CH=CH, $CH_2O$, $CH_2S(O)_m$, CH=N, or $CH_2NR^{10}$, where m=0–2; and
$R^{10}$=H, alkyl, acyl;
Z=H, alkyl, alkoxy, acyl, acyloxy, halo, trihalomethyl, amino, alkylamino, acylamino, or OH; and
⎯⎯⎯⎯=single or double bond.

13. The compound of claim 12, wherein for formula I:
$R^1$=$CO_2R$, where R=H or $CO_2R$ forms a pharmaceutically acceptable ester moiety;
n=0;
⎯⎯⎯⎯=a single bond between carbons 5 and 6, and a cis double bond between carbons 4 and 5;

$R^2$=$R^3$=H;
$R^9$=H;
J=O or H and H;
one of C,D=H, and the other=OH;
X=$CH_2O$ or $CH_2CH_2$; and
Y=phenyl, optionally substituted with halo or trihalomethyl; or
X-Y=$Y^1$, where

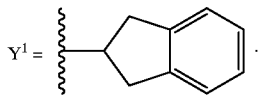

14. The compound of claim 13, having the formula:

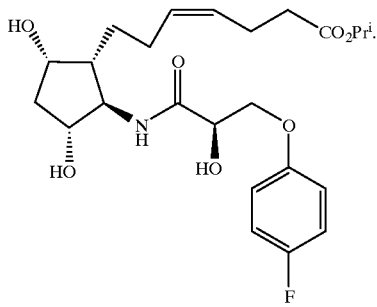

15. A compound having the formula:

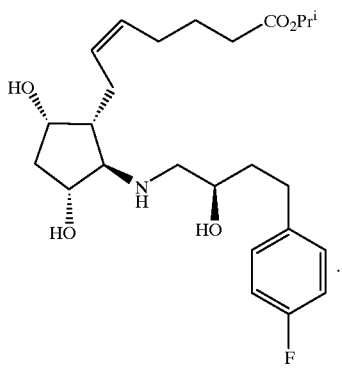

16. An ophthalmic composition for the treatment of glaucoma and ocular hypertension, comprising a compound of formula I:

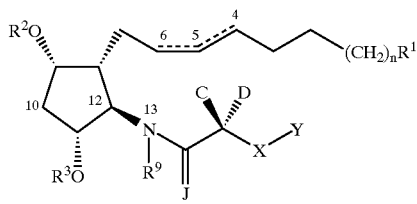

wherein:
$R^1$=$CO_2R$, $CONR^4R^5$, $CH_2OR^6$, or $CH_2NR^7R^8$, where:
R=H, alkyl, cationic salt moiety, or $CO_2R$ forms a pharmaceutically acceptable ester moiety;
$R^4$, $R^5$=same or different=H or alkyl; <$R^6$=H, acyl, or alkyl;

R⁷, R⁸=same or different=H, acyl, or alkyl; with the proviso that if one of R⁷, R⁸=acyl, then the other=H or alkyl;

n=0 or 2;

R², R³=same or different=H, alkyl, or acyl;

———=a single bond between carbons 5 and 6, and a cis double bond between carbons 4 and 5;

J=O, or H and H;

R⁹=H, alkyl, acyl, or SO₂Ar, where Ar=a phenyl ring optionally substituted with hydroxy, acyloxy, alkoxy, alkoxycarbonyl, halo, trihalomethyl, amino, acylamino, or aminoacyl;

one of C, D=H, the other=F, OH, acyloxy, or alkoxy; or C—D=O(CH₂)₂O or double bonded O;

with the proviso that if J=O, then R⁹=H or alkyl, one of C, D=H, and the other=F, OH, acyloxy, or alkoxy;

X=(CH₂)$_q$, (CH₂)$_q$O, where q=0–6; and

Y=a phenyl ring optionally substituted with alkyl, halo, trihalomethyl, alkoxy, acyl, acyloxy, alkylamino, acylamino, or OH;

or X-Y=(CH₂)$_p$Y¹, where p=0–6; and

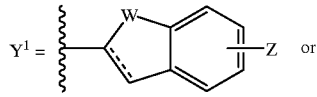

or

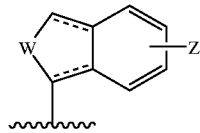

wherein:

W=CH₂, O, S(O)$_m$, NR¹⁰, CH₂CH₂, CH=CH, CH₂O, CH₂S(O)$_m$, CH=N, or CH₂NR¹⁰, where m=0–2; and R¹⁰=H, alkyl, or acyl;

Z=H, alkyl, alkoxy, acyl, acyloxy, halo, trihalomethyl, amino, alkylamino, acylamino, or OH; and ———=single or double bond;

and an ophthalmically acceptable vehicle therefor.

17. The composition of claim 16, wherein for the compound of formula I:

R¹=CO₂R, where R=H or CO₂R forms a pharmaceutically acceptable ester moiety;

n=0;

———=a single bond between carbons 5 and 6, and a cis double bond between carbons 4 and 5;

R²=R³=H;

R⁹=H;

J=O or H and H;

one of C,D=H, and the other=OH;

X=CH₂O or CH₂CH₂; and

Y=phenyl, optionally substituted with halo or trihalomethyl; or

X-Y=Y¹, where

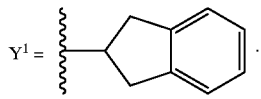

18. The composition of claim 17, wherein the compound has the following formula:

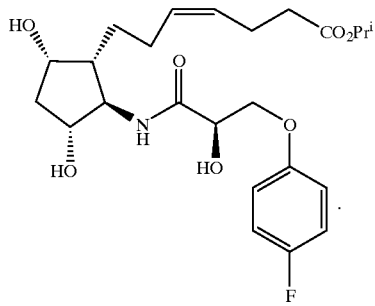

19. An ophthalmic composition for the treatment of glaucoma and ocular hypertension, comprising a compound having the formula:

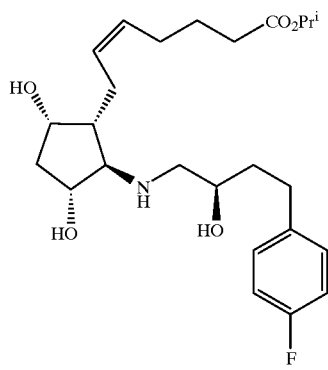

and an ophthalmically acceptable vehicle therefor.

* * * * *